United States Patent
Cho et al.

(10) Patent No.: US 10,300,063 B2
(45) Date of Patent: May 28, 2019

(54) PHARMACEUTICAL COMPOSITION NOT CONTAINING ANTIOXIDANT AND PREPARATION METHOD THEREFOR

(71) Applicant: SAMYANG BIOPHARMACEUTICALS CORPORATION, Seoul (KR)

(72) Inventors: Joong-Woong Cho, Daejeon (KR); Gyeong-Hae Kim, Daejeon (KR); Min-Hyo Seo, Daejeon (KR); Sa-Won Lee, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 15/108,810

(22) PCT Filed: Dec. 26, 2014

(86) PCT No.: PCT/KR2014/012886
§ 371 (c)(1),
(2) Date: Jun. 29, 2016

(87) PCT Pub. No.: WO2015/102315
PCT Pub. Date: Jul. 9, 2015

(65) Prior Publication Data
US 2016/0317539 A1 Nov. 3, 2016

(30) Foreign Application Priority Data

Dec. 30, 2013 (KR) ........................ 10-2013-0167677

(51) Int. Cl.
| | | |
|---|---|---|
| *B01D 19/00* | (2006.01) |
| *C02F 1/20* | (2006.01) |
| *C02F 1/22* | (2006.01) |
| *A61K 31/519* | (2006.01) |
| *A61K 9/19* | (2006.01) |
| *A61K 9/08* | (2006.01) |
| *A61K 47/26* | (2006.01) |

(52) U.S. Cl.
CPC .............. *A61K 31/519* (2013.01); *A61K 9/08* (2013.01); *A61K 9/19* (2013.01); *A61K 47/26* (2013.01)

(58) Field of Classification Search
CPC ....... B01D 19/0036; B01D 19/00; C02F 1/20; C02F 1/22
See application file for complete search history.

(56) References Cited

U.S. PATENT DOCUMENTS

| | | | | |
|---|---|---|---|---|
| 6,686,365 B2* | 2/2004 | Riebesehl | ............... | A61K 45/06 514/262.1 |
| 2007/0077303 A1* | 4/2007 | Alli | ...................... | A61K 9/0048 424/486 |
| 2009/0044700 A1* | 2/2009 | Dietlin | .................. | A23L 3/3436 95/30 |
| 2009/0181990 A1 | 7/2009 | Patel | | |
| 2013/0231357 A1 | 9/2013 | Palepu | | |

FOREIGN PATENT DOCUMENTS

| | | | |
|---|---|---|---|
| CN | 101411710 | | 4/2009 |
| CN | 103432086 | | 12/2013 |
| JP | 55-106231 | | 8/1980 |
| JP | 2007-045791 | | 2/2007 |
| KR | 10-1069128 | | 9/2011 |
| KR | 10-1069128 B | * | 9/2011 |
| KR | 10-1260636 | | 4/2013 |
| KR | 10-2013-0122065 | | 11/2013 |
| WO | 01/56575 | | 8/2001 |
| WO | 2008/021411 | | 2/2008 |
| WO | 2010/030598 | | 3/2010 |
| WO | 2012/121523 | | 9/2012 |
| WO | WO-2012121523 A2 | * | 9/2012 ........... A61K 31/519 |
| WO | 2013/144814 | | 10/2013 |
| WO | 2014/060962 | | 4/2014 |

OTHER PUBLICATIONS

Zhang et al. ("Physical stability of frozen pemetrexed solutions in PVC bags", The Annual Pharmacotherapy, Jul./Aug. 2006, vol. 40, 1289-1292.*
Rollie, Mae E., Gabor Patonay, and Isiah M. Warner. "Deoxygenation of solutions and its analytical applications." Industrial & engineering chemistry research 26.1 (1987): 1-6.*
Butler, Ian B., Martin AA Schoonen, and David T. Rickard. "Removal of dissolved oxygen from water: a comparison of four common techniques." Talanta 41.2 (1994): 211-215.*
N. Barboy and J. Foiteleon, Deoxygenation of Solutions for Transient Studies:, Anal Biochem, 1989, vol. 180, pp. 384-386.
Julian Eastoe et al., "De-gassed water and surfactant-ft-ee emulsions: History, controversy, and possible applications", Adv Colloid Interface Sci, 2007, vol. 134-135, pp. 89-95.
EPO, Extended European Search Report of EP 14877377.3 dated Jul. 10, 2017.
Yanping Zhang, et al., "Physical instability of frozen pemetrexed solutions in PVC bags." The Annals of pharmacotherapy, vol. 40, Issue 7-8, Jul. 5, 2006(Online Published), pp. 1289-1292.

(Continued)

*Primary Examiner* — Bethany P Barham
*Assistant Examiner* — Peter Anthopolos
(74) *Attorney, Agent, or Firm* — Lex IP Meister, PLLC

(57) ABSTRACT

Provided are a composition containing an unstable drug against oxidation like pemetrexed with improved stability and a preparation method thereof, by removing oxygen during the preparation without use of an antioxidant. The method is readily applicable for manufacturing by freezing and degassing in a sealed chamber, and can provide formulations with significantly increased stability for the unstable drug against oxidation.

8 Claims, No Drawings

(56) References Cited

OTHER PUBLICATIONS

"SOP—Freeze-Pump-Thaw Degassing of Liquids", Safety Web, Standard Operating Procedure: Freeze-Pump-Thaw Degassing of Liquids, Oregon State University, Web Apr. 13, 2011.
Sarah Millar, "Tips and Tricks for the Lab: Air-Sensitive Techniques (2)", Education, Chemistry Views, Web Jun. 4, 2013.
D.F. Shriver et al., "The Manipularion of Air-Sensitive Compounds", 1986.
Timothy D W Claridge, "High-Resolution NMR Techniques in Organic Chemistry", Tetrahedron Organic Chemistry Series, vol. 19, 1999.
Edvard Hemmingsen, "Permeation of Gases through Ice", Tellus, vol. 11, No. 3, 1958.
EPO, Communication pursuant to Rule 114(2) EPC of EP 14877377.3 dated on Apr. 8, 2019.

\* cited by examiner

PHARMACEUTICAL COMPOSITION NOT CONTAINING ANTIOXIDANT AND PREPARATION METHOD THEREFOR

TECHNICAL FIELD

The present disclosure relates to a pharmaceutical composition with improved stability, including pemetrexed or pharmaceutically acceptable salts thereof, and a preparation method thereof.

BACKGROUND ART

Pemetrexed disodium is a new multitargeted antifolate with excellent anti-cancer activity applied to various solid cancers such as non-small cell lung cancer (NSCLC), malignant pleural mesothelioma, breast cancer, colon cancer, uterine cancer, head and neck cancer, and bladder cancer. Alimta (trademark) has been used in the clinical field as a lyophilized injectable formulation. Alimta is administered in combination with cisplatin to a patient with malignant pleural mesothelioma who has not been received chemotherapy and is not eligible for surgery. Since 2007, it has also been used as a single administration to locally advanced breast cancer or NSCLC patients after chemotherapy.

Most lyophilized injectable formulations are currently used by preparing a lyophilized powder due to the instability of a drug in an aqueous solution and reconstituting the powder with physiological saline or water for injection before injection to a patient. However, the reconstitution is a cumbersome process in that a desired amount of saline or water should be weighed and poured into a vial, and has the risk of microbial contamination and a limitation in that the reconstituted formulation must be used within a certain period of time. Further, the lyophilized formulation has a high production cost and a complex manufacturing process due to a long drying cycle during the lyophilization. Therefore, in considering the production cost and user convenience, there is a need for a ready-to-use liquid formulation with stability.

However, pemetrexed is rapidly oxidized in an aqueous solution and as a result, produces various related compounds. For a drug unstable in liquid, a representative method of increasing the stability thereof is to add an antioxidant or to remove dissolved oxygen. As examples of using an antioxidant, WO2001/56575 discloses a liquid formulation including pemetrexed and an antioxidant such as monothioglycerol, L-cysteine, or thioglycolic acid. KR 10-1260636 discloses that acetyl cysteine is used as an antioxidant and citric acid is used as a buffering agent, so as to provide a formulation with increased stability for pemetrexed. However, it would be preferable to minimize the use of additives for preparing a medicine for its safety. Particularly, unidentified degradation products caused from the antioxidant and oxidative degradation products of the antioxidant itself may be formed. WO2012/121523 discloses a preparation method to increase stability by controlling dissolved oxygen concentration (DOC) in an injectable solution to be 1 ppm or lower without using an antioxidant. However, the preparation method disclosed in the document can be carried out in a lab scale but has many difficulties in a commercial scale. Particularly, in the case that water for injection or an aqueous solution, which has been degassed, is dispensed into a glass vial in a commercial scale, it is very difficult to maintain the degassed state. Therefore, the process could prevent oxidation to increase stability without using an antioxidant, but could hardly be scaled up to a commercial manufacturing process.

DISCLOSURE

Technical Problem

In consideration of the problems in the art, one object of the present invention is to provide an antioxidant-free pharmaceutical composition with stability in an aqueous solution, and a preparation method thereof, which method can be applied for commercial production in a large scale, by performing all steps in a sealed chamber without using a stabilizing agent such as an antioxidant.

Another object of the present invention is to provide a pharmaceutical composition with improved stability and a preparation method thereof, by removing oxygen without using an antioxidant.

Still another object of the present invention is to provide a pharmaceutical composition with improved stability including pemetrexed and a preparation method thereof, which method is performed by simply carrying out freezing and degassing in a sealed chamber, neither using an antioxidant nor preparing the composition from an aqueous solution that has been degassed in a sealed system, thereby obtaining stability of the drug unstable against oxidation as well as being applicable for commercial production in a large scale.

Technical Solution

To resolve the problems, an embodiment of the present invention provides a method of preparing an antioxidant-free pharmaceutical composition, including: (a) freezing a solution including pemetrexed or a pharmaceutically acceptable salt thereof and an aqueous solvent to obtaining a frozen product; and (b) degassing the frozen product under reduced pressure to obtain a degassed and frozen product.

Another embodiment of the present invention provides an antioxidant-free pharmaceutical composition including pemetrexed or a pharmaceutically acceptable salt thereof and an aqueous solvent that is frozen and degassed.

The solution of step (a) can be a solution which has not been degassed, and can be frozen at −20° C. or lower. The degassed and frozen product may include a solvent in an amount of 95 to 100 parts by weight, with respect to 100 parts by weight of the solvent contained in the solution of step (a), and the degassing may be performed to 1.5 ppm or less of DOC in step (b).

Preferably, the freezing, the degassing, and optionally a sealing may be carried out in a sealed chamber. The method may further include thawing the degassed and frozen product after step (b) or the sealing step. The pressure of step (b) may be 2,000 mTorr or lower.

The composition may further include one or more selected from the group consisting of pharmaceutically acceptable excipients and pH adjusting agents, for example, mannitol as the excipient, or hydrochloric acid, sodium hydroxide, or a mixture thereof as the pH adjusting agent.

An embodiment of the present invention relates to a method of reducing a dissolved oxygen concentration of an antioxidant-free pharmaceutical composition, including: (a) freezing a composition containing an aqueous solvent and pemetrexed or a pharmaceutically acceptable salt thereof to produce a frozen product; and (b) degassing the frozen product under reduced pressure to obtain a degassed and frozen product.

Another embodiment of the present invention relates to a method of stabilizing an antioxidant-free pharmaceutical composition, including: (a) freezing a composition containing an aqueous solvent and pemetrexed or a pharmaceutically acceptable salt thereof to produce a frozen product; and (b) degassing the frozen product under reduced pressure to obtain a degassed and frozen product.

A preferred embodiment of the present invention relates to a method of increasing stability of a drug unstable against oxidation by removing dissolved oxygen in an aqueous solution without using an antioxidant, including: (a) freezing a composition containing an aqueous solvent and pemetrexed or a pharmaceutically acceptable salt thereof to produce a frozen product; and (b) degassing the frozen product under reduced pressure to obtain a degassed and frozen product, in a sealed chamber, or (a) freezing a composition containing an aqueous solvent and pemetrexed or a pharmaceutically acceptable salt thereof to produce a frozen product, (b) degassing the frozen product under reduced pressure to obtain a degassed and frozen product, and (c) sealing the degassed and frozen product, in a sealed chamber.

The present invention employs degassing for increasing stability of a drug unstable against oxidation, which removes oxygen in an aqueous solution without using an antioxidant, thereby to minimize the use of additives for manufacturing a medicine, and prevent the production of unidentified degradation products caused from the antioxidant and oxidative degradation products of the antioxidant itself. Preferably, because the degassing is carried out in a sealed chamber, it can be easily performed in a sterile chamber without contamination. Therefore, the degassing step of the present invention has various advantages in time, convenience, and production yield, compared to the prior degassing step.

The present invention will be explained in more detail.

An embodiment of the present invention provides a method of preparing an antioxidant-free pharmaceutical composition with excellent stability on a commercial scale, including: freezing a composition containing an aqueous solvent and pemetrexed or a pharmaceutically acceptable salt thereof to produce a frozen product; and (b) degassing the frozen product under reduced pressure, e.g. in vacuum, to obtain a degassed and frozen product.

Another embodiment of present invention relates to an antioxidant-free pharmaceutical composition including an aqueous solvent and pemetrexed, or a pharmaceutically acceptable salt thereof that is frozen and degassed. The pharmaceutical composition may be thawed and used as a liquid parenteral formulation, specifically a liquid injectable formulation.

In general, an injectable formulation including pemetrexed cannot be stabilized by filling an inert gas such as nitrogen to a head space, but by adding an antioxidant thereto. However, as the use of additives for medicines should be preferably minimized in an aspect of safety, the present invention provides a method of preparing a liquid pharmaceutical composition with improved stability without using a stabilizing agent such as an antioxidant.

In step (a), a solution including pemetrexed or a pharmaceutically acceptable salt and an aqueous solvent can be prepared and frozen to produce a frozen product. The freezing step can be performed after a solution including pemetrexed or a pharmaceutically acceptable salt and an aqueous solvent is prepared. The solution can be dispensed into a filling container before the freezing step. The solution of step (a) is pourted into a container such as an ampoule or a vial, and then the freezing, the degassing, and the sealing can be carried out continuously in a sealed chamber, thereby making the method be advantageous in maintaining the degassed state during large-scale production.

In the present invention, the term "pemetrexed" is a 5-substituted pyrrolo[2,3-d]pyrimidine as represented by Chemical Formula 1, and is a multitargeted antifolate with anti-cancer activity applied to various solid cancers such as non-small cell lung cancer (NSCLC), malignant pleural mesothelioma, and the like.

Chemical Formula 1

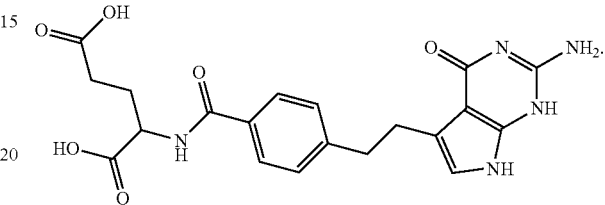

In the present invention, the term "pharmaceutically acceptable salts" refers to salts prepared according to conventional methods in the art. Specifically, the pharmaceutically acceptable salts include salts derived from inorganic acids, organic acids, and bases that are pharmaceutically acceptable, but are not limited thereto. Examples of suitable acids are hydrochloric acid, bromic acid, hydrobromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzene sulfonic acid, and the like. Examples of suitable bases include alkali metals such as sodium or potassium, and alkaline earth metals such as magnesium, but are not limited to thereto. In particular, a pharmaceutically acceptable salt of pemetrexed can be pemetrexed disodium, but is not limited thereto.

In the present invention, the term "pemetrexed or pharmaceutically acceptable salts thereof" includes hydrates of pemetrexed or pharmaceutically acceptable salts thereof, and includes any types of hydrates, for example, 2.5-hydrate, 7-hydrate, etc., but are not limited thereto.

The aqueous solvent may be a buffer solution, preferably water, for example, water for injection or physiological saline.

The pharmaceutical composition according to the present invention may include one or more selected from the group consisting of a pharmaceutically acceptable excipient and a pH adjusting agent, and for example, the excipient may be mannitol, and the pH adjusting agent may be hydrochloric acid, sodium hydroxide, or a mixture thereof. The excipient and the pH adjusting agent may be added to the solution of step (a).

A solution or a solvent of step (a) may be one that has not been degassed. In order to control the dissolved oxygen concentration in liquid formulations, the prior-art method should include a step of controlling the dissolved oxygen concentration for an aqueous solvent itself or a solution containing a drug dissolved in the aqueous solvent. However, the present invention does not require the step of degassing or controlling the dissolved oxygen concentration for the aqueous solvent itself or the solution containing a drug dissolved in the aqueous solvent, because the degassing step is performed after a freezing step. According to the present invention, a highly stable liquid formulation can be easily and simply prepared.

The freezing of the solution in step (a) can be performed at a temperature of −20° C. or lower, preferably −30° C. or lower, for example −50° C. to −30° C., particularly −40° C. Any freezing method of liquid formulations can be applied for the present invention.

The degassed and frozen product of step (b) may include a solvent in an amount of 95 to 100 parts by weight or more, preferably 98 to 100 parts by weight, with respect to 100 parts by weight of the solvent contained in the solution of step (a). The most solvent in the degassed and frozen product may be maintained after degassing the frozen product. Thus, the degassed and frozen product may be a liquid composition when thawed, and may be used directly without a reconstitution step. Unlike the conventional lyophilized powder preparations, the pharmaceutical composition is prepared by performing a degassing step to control the dissolved oxygen concentration in step (b) but not a drying step to remove the solvent, thereby stabilizing pemetrexed or pharmaceutically acceptable salts unstable against oxidation.

The dissolved oxygen concentration of the degassed and frozen product obtained in step (b) or the thawed product thereafter may be 1.5 ppm or less. The stability of oxygen-labile pemetrexed or a pharmaceutically acceptable salt can be obtained by reducing the dissolved oxygen concentration in the pharmaceutical composition by performing the degassing step.

In another embodiment of the present invention, the freezing and degassing steps, and preferably a sealing step, in the method of preparing the pharmaceutical composition, can be carried out in a sealed chamber. Specifically, the solution of step (a) may be frozen at a temperature of −20° C. or lower, and the frozen product may be degassed under reduced pressure and sealed immediately thereafter. Therefore, the freezing, the degassing, and the sealing are performed continuously in one chamber.

In an embodiment of present invention, the method can further include filling nitrogen into the container filled with the composition, before the sealing step and after the freezing of step (a) and the degassing of step (b). In order to prevent the occurrence of air backflow due to negative pressure caused by the vacuum in the head space of the filled container, the negative pressure is reduced by filling nitrogen into the container filled with the composition before the sealing step and after the degassing step, so as to largely decrease the risk of air backflow. Specifically, the method can further include de-vacuumizing by filling nitrogen before sealing the container with a rubber stopper. The dissolved oxygen is not sufficiently removed or air can be penetrated even through small pores if the negative pressure is maintained in the vial, although the sealing step after degassing and the de-vacuumizing step are performed. Therefore, the nitrogen filling before the sealing step can significantly decrease the negative pressure inside the vial, thereby reducing the risk.

In general, vacuumization in a liquid state causes boiling-over of the liquid by vapor pressure, but the vacuumization in a frozen state can remove gas with a lower freezing point than an aqueous solution before occurrence of drying without causing loss of components and contents of the composition. On the basis of this fact, the inventors developed a method of degassing the frozen product of an aqueous solution in a sealed chamber.

Herein, the term "degassing" refers to removal of gas molecules from a solid or liquid. The basic principle of removing the gas molecules is based on Henry's law and Dalton's law on partial pressure. Henry's law states that the amount of dissolved gas in solution is proportional to its partial pressure in a gas contacting the solution. The decrease of pressure in the gas contacting the solution, e.g. vacuum, causes the gas molecules to be discharged from the liquid. Alternatively, by using the principle that the saturation degree of a dissolved gas depends on the temperature of a liquid, heating of the liquid causes the gas molecules to be discharged from the liquid. The method of liquid heating requires energy consumption for heating the liquid, and cannot be suitable for medicines because of denaturation or concentration change of heat-labile drugs or excipients. Various degassing methods such as membrane degassing and catalytic resin degassing are used as well, but cannot be applied to the production due to many difficulties such as a complex production process. Such degassing step can block the oxidative reaction by significantly decreasing the dissolved oxygen concentration in an aqueous solution.

The degassing of step (b) can be carried out under a certain range of pressure, and for example, the upper limit of the pressure may be 2,000 mTorr, preferably 1,000 mTorr, or more preferably 500 mTorr, for example 300 mTorr. The lower limit of the pressure may be 0 mTorr, or preferably 5 mTorr, for example 100 mTorr. The degassing is performed to maintain the desired degree of vacuum for a predetermined period of time after achieving the desired degree of vacuum, thereby removing oxygen or oxygen-containing gas from the frozen product.

The present invention is distinguishable from a typical freeze-drying process in that the vacuum is released prior to occurrence of drying, when the desired vacuum state is achieved by reducing the pressure. This is because the concentration of the active ingredient increases due to the reduction of the solvent as the drying proceeds. To prevent the drying in advance, the degree of vacuum after achieving the desired degree of vacuum is maintained for 12 hours or shorter, more preferably 10 hours or shorter, or most preferably 6 hours or shorter. For example, the sealing and/or the vacuum relief may be performed immediately (0 hour) after achieving the desired degree of reduced pressure.

The solvent in the degassed and frozen composition or the thawed liquid composition may be ideally maintained in an amount of 100 parts by weight, preferably 95 to 100 parts by weight, or more preferably 98 to 100 parts by weight, with respect to 100 parts by weight of the solvent in the solution prior to the degassing step.

In addition, the thawing step can be carried out by increasing the temperature in the sealed chamber, or outside of the sealed chamber. Preferably, it is avoided to take out the vial from the sealed chamber at a too low temperature, because moisture formed on the surface of the vial may make aluminum capping troublesome.

The liquid pharmaceutical composition obtained in the preparation method of the present invention can be sterilized according to any method such as sterilized filtration and/or heat sterilization. In addition, the aqueous solvent or the solution in step (a) of the present invention can be sterilized according to any method such as sterilized filtration and/or heat sterilization.

Advantageous Effect

The pharmaceutical composition of the present invention can minimize the use of additives by not using an antioxidant, and exclude fundamentally unidentified degradation products caused from the antioxidant and oxidative degradation products of the antioxidant itself.

In addition, the preparation method of the present invention is suitable for a large-scale production, and is a simple method performed in a sterile chamber without contamination, because the freezing, the degassing, and the sealing can be performed continuously in a sealed chamber. The method is efficient in aspects of time, convenience, and production yield, compared to the prior degassing method.

DETAILED DESCRIPTION OF THE EMBODIMENTS

The present invention will be described in more detail with reference to the following examples. However, these examples are for illustrative purposes only, and the invention is not intended to be limited by these examples.

[Examples 1 to 5] Preparation of Liquid Formulations with Various Vacuum Degrees (1) Preparation of Mixed Solution Filled in Vials 48.3 g (40 g as pemetrexed) of pemetrexed disodium 2.5-hydrate was dissolved completely in 1500 ml of water for injection and 40 g of mannitol was added thereto and completely dissolved. To the obtained solution was added 0.1N HCl to adjust the pH to 7.3, and water for injection was added thereto to adjust a total weight of the mixed solution to 1,600 g. DOC of the mixed solution was about 7.0 ppm. The mixed solution was filtered with a sterile filter, filled into 5 ml vials to be 4 ml per vial in a clean bench, and the vials were sealed with rubber stoppers to obtain the mixed solution filled in the vials.

(2) Freezing and Degassing

The glass vials filled with the mixed solution were introduced into a sealed chamber with their rubber stopper slightly opened, and the solution was frozen at −40° C. for 1 hour. After confirming that the solution was completely frozen, vacuumization began by operating a vacuum pump in the sealed chamber, while maintaining the temperature of −40° C. The vacuum degree was controlled as shown in Table 1, and the vacuum pump was stopped immediately after the desired degree of vacuum reached and then the vials were sealed with rubber stoppers. The vacuum was released after confirming that the vials were sealed. The glass vials were taken out from the sealed chamber, and thawed and capped with aluminum caps. The DOC of the degassed and frozen formulation is shown in Table 1.

DOC was measured with an YSI 550A DOC analyzer with agitation in a glove box filled with nitrogen. The properties of the thawed solution are shown in Table 1.

TABLE 1

| | Concentration of active ingredient (mg/ml) | Vacuum degree (Torr) | DOC (ppm) | pH |
|---|---|---|---|---|
| Example 1 | 25 | 2 | 1.5 | 7.3 |
| Example 2 | 25 | 1 | 1.1 | 7.3 |
| Example 3 | 25 | 0.5 | 0.7 | 7.3 |
| Example 4 | 25 | 0.3 | 0.5 | 7.3 |
| Example 5 | 25 | 0.1 | 0.5 | 7.3 |

[Example 6] Preparation of Liquid Formulations by Freezing, Degassing, and Nitrogen-Filling The glass vials filled with the mixed solution were obtained according to the same method of Example 1. The glass vials filled with the mixed solution were introduced into a sealed chamber with their rubber stopper slightly opened, and the solution was frozen at −40° C. for 1 hour. After confirming that the solution was completely frozen, the vacuumization began by operating a vacuum pump in the sealed chamber, while maintaining the temperature of −40° C. The vacuum pump was stopped immediately after the degree of vacuum reached 300 mTorr, and the vials were filled with nitrogen and sealed with rubber stoppers. The vacuum was released after confirming that the vials were sealed. The glass vials were taken out from the sealed chamber, and were thawed and capped with aluminum caps. The DOC of the degassed and frozen formulation was about 0.5 ppm.

[Comparative Example 1] Preparation of Liquid Formulations without Freezing and Degassing The glass vials filled with the mixed solution were obtained according to the same method of Example 1. The vials were capped with aluminum caps. The DOC of the formulation was about 7.0 ppm.

[Comparative Example 2] Preparation of Liquid Formulations without Freezing and Degassing, but with Nitrogen-Filling The glass vials filled with the mixed solution were obtained according to the same method of Example 1. The vials were filled with nitrogen and sealed with rubber stoppers and capped with aluminum caps. The DOC of the formulation was about 7.0 ppm.

[Test Example 1] Accelerated Stability Test

The stability of formulations obtained in Examples 1 to 6 and Comparative Examples 1 and 2 was tested under an accelerated condition (40° C./75% RH). The stability test was performed by analyzing the appearance, pH, drug content, and amount of related compounds of the aqueous solution with HPLC.

A. HPLC Condition of Drug Content Analysis
  a. column: Zorbax SB-C8, 4.6 mm×150 mm, 3.5 μm, or column similar thereto
  b. detector: UV spectrophotometer (measuring wavelength: 285 nm)
  c. injection volume: 20 μl
  d. flow rate: 1.0 mL/min
  e. column temperature: 30° C.
  f. mobile phase: acetate buffer solution:acetonitrile=(89:11) (v/v %)*acetate buffer solution (30 mM, pH 5.3±1): Acetic anhydride was added to distilled water at a volume of 1.7 mL per 1 L of distilled water, and then, they were mixed together well, and a pH of the mixture was adjusted to 5.3±0.1 with the addition of 50% NaOH, and the mixture was filtered if necessary.

B. HPLC Condition of Related Compound Analysis
  a. column: Zorbax SB-C8, 4.6 mm×150 mm, 3.5 μm, or column similar thereto
  b. detector: UV spectrophotometer (measuring wavelength: 250 nm)
  c. injection volume: 20 μl
  d. flow rate: 1.0 mL/min
  e. column temperature: 25° C.
  f. auto-injector temperature: 2 to 8° C.
  g. mobile phase: gradient elution

TABLE 2

| Time (min) | Mobile phase A (%) | Mobile phase B (%) |
|---|---|---|
| 0 | 100 | 0 |
| 45 | 0 | 100 |
| 47 | 100 | 0 |
| 60 | 100 | 0 |

Mobile phase A: formate buffer solution:acetonitrile=95:5 (v/v)

Mobile phase B: formate buffer solution:acetonitrile=70:30 (v/v)

Formate buffer solution: 2.9 g of ammonium formate was dissolved in 2 L of distilled water, and a pH of the solution was adjusted to 3.5±0.1 with formic acid.

As shown above, the accelerated stability tests for the formulations of the examples and comparative examples (40° C./75% RH) were carried out for 12 weeks, and the results are shown in Table 3. The qualification standards were pH of 6.6 to 7.8, drug content of 95 to 105%, 1.5% or lower of total related compounds, and 0.2% or lower of individual related compound.

TABLE 3

| | Time (week) | Appearance | pH | Drug content (%) | Total related compounds (%) | Individual related compound (%) |
|---|---|---|---|---|---|---|
| Example 1 | 0 | colorless | 7.3 | 103.2 | 0.04 | 0.04 |
| | 1 | slightly light yellow | 7.3 | 99.5 | 0.65 | 0.48 |
| | 2 | light yellow | 7.3 | 91.7 | 2.15 | 0.99 |
| | 3 | yellow | 7.2 | 88.1 | 4.88 | 2.11 |
| | 4 | yellow | 7.1 | 84.7 | 7.66 | 3.77 |
| | 8 | yellow | 7.1 | 82.3 | 12.60 | 5.52 |
| | 12 | dark yellow | 7.0 | 74.0 | 15.33 | 6.89 |
| Example 2 | 0 | colorless | 7.3 | 102.4 | 0.04 | 0.04 |
| | 1 | slightly light yellow | 7.3 | 100.3 | 0.07 | 0.05 |
| | 2 | slightly light yellow | 7.2 | 99.1 | 0.15 | 0.10 |
| | 3 | slightly light yellow | 7.3 | 99.2 | 0.96 | 0.46 |
| | 4 | light yellow | 7.2 | 98.2 | 1.25 | 0.56 |
| | 8 | light yellow | 7.2 | 96.7 | 2.33 | 0.96 |
| | 12 | yellow | 7.1 | 95.3 | 3.05 | 1.38 |
| Example 3 | 0 | colorless | 7.3 | 102.1 | 0.04 | 0.04 |
| | 1 | slightly light yellow | 7.3 | 101.4 | 0.05 | 0.05 |
| | 2 | slightly light yellow | 7.3 | 102.5 | 0.06 | 0.06 |
| | 3 | slightly light yellow | 7.3 | 101.8 | 0.09 | 0.06 |
| | 4 | slightly light yellow | 7.2 | 101.4 | 0.12 | 0.07 |
| | 8 | slightly light yellow | 7.2 | 100.1 | 0.16 | 0.10 |
| | 12 | slightly light yellow | 7.2 | 100.6 | 0.21 | 0.12 |
| Example 4 | 0 | colorless | 7.3 | 103.3 | 0.05 | 0.05 |
| | 1 | colorless | 7.3 | 103.3 | 0.05 | 0.05 |
| | 2 | slightly light yellow | 7.3 | 103.0 | 0.06 | 0.05 |
| | 3 | slightly light yellow | 7.3 | 102.5 | 0.06 | 0.05 |
| | 4 | slightly light yellow | 7.3 | 102.6 | 0.11 | 0.06 |
| | 8 | slightly light yellow | 7.1 | 101.1 | 0.12 | 0.07 |
| | 12 | slightly light yellow | 7.2 | 101.6 | 0.15 | 0.08 |
| Example 5 | 0 | colorless | 7.3 | 102.7 | 0.05 | 0.05 |
| | 1 | colorless | 7.3 | 103.4 | 0.05 | 0.05 |
| | 2 | slightly light yellow | 7.3 | 102.1 | 0.05 | 0.05 |
| | 3 | slightly light yellow | 7.2 | 102.2 | 0.06 | 0.06 |
| | 4 | slightly light yellow | 7.2 | 102.0 | 0.10 | 0.06 |
| | 8 | slightly light yellow | 7.2 | 101.7 | 0.13 | 0.07 |
| | 12 | slightly light yellow | 7.2 | 101.5 | 0.16 | 0.09 |
| Example 6 | 0 | colorless | 7.3 | 103.1 | 0.05 | 0.05 |
| | 1 | colorless | 7.3 | 102.4 | 0.05 | 0.05 |
| | 2 | slightly light yellow | 7.2 | 102.1 | 0.05 | 0.05 |
| | 3 | slightly light yellow | 7.3 | 101.1 | 0.06 | 0.06 |
| | 4 | slightly light yellow | 7.2 | 101.8 | 0.10 | 0.06 |
| | 8 | slightly light yellow | 7.1 | 102.1 | 0.12 | 0.07 |
| | 12 | slightly light yellow | 7.2 | 101.6 | 0.14 | 0.08 |

TABLE 3-continued

| | Time (week) | Appearance | pH | Drug content (%) | Total related compounds (%) | Individual related compound (%) |
|---|---|---|---|---|---|---|
| Comparative Example 1 | 0 | colorless | 7.3 | 103.5 | 0.05 | 0.05 |
| | 1 | slightly light yellow | 7.2 | 97.5 | 0.90 | 0.52 |
| | 2 | light yellow | 7.2 | 91.0 | 3.05 | 1.33 |
| | 3 | yellow | 7.1 | 84.1 | 9.09 | 4.84 |
| | 4 | yellow | 7.1 | 78.2 | 11.72 | 5.42 |
| | 8 | dark yellow | 7.0 | 71.5 | 16.20 | 6.10 |
| | 12 | dark yellow | 6.9 | 61.9 | 18.56 | 7.14 |
| Comparative Example 2 | 0 | colorless | 7.3 | 102.9 | 0.05 | 0.05 |
| | 1 | slightly light yellow | 7.3 | 99.1 | 0.76 | 0.53 |
| | 2 | light yellow | 7.2 | 95.7 | 2.52 | 1.11 |
| | 3 | yellow | 7.2 | 82.2 | 8.09 | 2.84 |
| | 4 | yellow | 7.1 | 79.2 | 12.72 | 4.29 |
| | 8 | dark yellow | 7.1 | 72.8 | 15.01 | 6.00 |
| | 12 | dark yellow | 7.0 | 66.5 | 17.56 | 6.84 |

As a result of tests, the formulations of Examples 3 to 6 showed similar test results, and it was presumed that the degassing was achieved in a similar level under the vacuum degrees of 500 mTorr or lower. The formulations of comparative examples without degassing showed significantly lower stability irrespective of nitrogen-filling. This shows that the process of removing the dissolved oxygen by degassing significantly improves the stability of pemetrexed.

[Test Example 2] Stress Stability Test

The stability of formulations obtained in Example 5 and Comparative Example 1 was tested under a stressed condition (60° C./80% RH) for 4 weeks. The stability test results are shown in Table 4.

TABLE 4

| | Time (week) | Appearance | pH | Drug content (%) | Total related compounds (%) | Individual related compound (%) |
|---|---|---|---|---|---|---|
| Example 5 | 0 | colorless | 7.2 | 102.1 | 0.05 | 0.05 |
| | 1 | colorless | 7.2 | 101.2 | 0.07 | 0.05 |
| | 2 | slightly light yellow | 7.2 | 101.6 | 0.16 | 0.07 |
| | 3 | slightly light yellow | 7.1 | 100.5 | 0.22 | 0.09 |
| | 4 | light yellow | 7.1 | 101.0 | 0.29 | 0.12 |
| Comparative Example 1 | 0 | colorless | 7.2 | 102.5 | 0.05 | 0.05 |
| | 1 | slightly light yellow | 7.1 | 87.9 | 7.91 | 3.81 |
| | 2 | light yellow | 7.1 | 75.9 | 10.22 | 4.97 |
| | 3 | yellow | 7.0 | 67.0 | 17.35 | 7.46 |
| | 4 | dark yellow | 6.9 | 56.9 | 27.23 | 12.22 |

As a result of the test, the formulation of Example 5 showed a slightly changed appearance after 1 month, but little changed drug content and the total related compounds (1.5% or lower), and individual related compound (0.2% or lower) satisfying the qualification standards. However, the formulation of Comparative Example 1 not degassed showed the drug content and related compounds deviated from the qualification standards and turned dark brown only in 1 week, which indicated the considerable occurrence of oxidation. This shows that the aqueous solution formulation with improved stability prepared by degassing is such a stable formulation that can be stored at room temperature.

The invention claimed is:

1. A method of preparing an antioxidant-free pharmaceutical composition, comprising:

(a) preparing an antioxidant-free solution with dissolved oxygen comprising pemetrexed or a pharmaceutically acceptable salt thereof, and an aqueous solvent in a container;
(b) freezing the antioxidant-free solution in the container to produce a frozen product; and
(c) degassing the frozen product under a pressure of 2,000 mTorr or lower to obtain a degassed and frozen product, wherein the degassed and frozen product comprises 95 to 100 parts by weight of the solvent per 100 parts by weight of the solvent contained in the solution of step (a), and the steps of (b) and (c) are performed at a temperature of −20° C. or tower in a sealed chamber.

2. The method of claim 1, wherein the degassing in step (c) is performed to have a concentration of the dissolved oxygen to be 1.5 ppm or lower.

3. The method of claim 1, wherein the degassing in step (c) is performed for 12 hours or shorter.

4. The method of claim 1, wherein the solution further comprises at least one selected from the group consisting of (i) pharmaceutically acceptable excipients excluding antioxidants and (ii) pH adjusting agents.

5. The method of claim 4, wherein the excipient is mannitol, or the pH adjusting agent is hydrochloric acid, sodium hydroxide, or a mixture thereof.

6. The method of claim 1, wherein the method further comprises a step of sealing the container or a step of filling the container with nitrogen followed by sealing, after step (c).

7. The method of claim 1, wherein the method further comprises thawing the degassed and frozen product, after step (c).

8. The method of claim 6, wherein the method further comprises thawing the degassed and frozen product, after the sealing the container.

* * * * *